(12) United States Patent
Roach et al.

(10) Patent No.: US 8,099,851 B2
(45) Date of Patent: Jan. 24, 2012

(54) CRIMPING AND EDGE PROTECTION ELEMENTS

(75) Inventors: Tina Roach, Elk River, MN (US); Jon Livingston, Maple Grove, MN (US); Beccie McCarville, Spring Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1971 days.

(21) Appl. No.: 11/167,507

(22) Filed: Jun. 27, 2005

(65) Prior Publication Data

US 2006/0288561 A1    Dec. 28, 2006

(51) Int. Cl.
*B23P 11/00*    (2006.01)
*B21D 37/10*    (2006.01)

(52) U.S. Cl. ............... 29/516; 72/402; 72/416; 72/357; 29/282; 29/508

(58) Field of Classification Search .............. 29/516, 29/508, 283.5, 282, 234; 72/402, 416, 357, 72/414
See application file for complete search history.

(56) References Cited

U.S. PATENT DOCUMENTS

| | | | |
|---|---|---|---|
| 5,992,000 A | 11/1999 | Humphrey et al. ............ 29/516 |
| 6,063,092 A | 5/2000 | Shin ............... 606/108 |
| 6,063,102 A | 5/2000 | Morales ............ 606/198 |
| 6,074,381 A | 6/2000 | Dinh et al. ............ 606/1 |
| 6,082,990 A | 7/2000 | Jackson et al. ............ 425/517 |
| 6,092,273 A | 7/2000 | Villareal ............ 29/516 |
| 6,108,886 A | 8/2000 | Kimes et al. ............ 29/280 |
| 6,168,921 B1 | 1/2001 | Riss et al. ............ 435/6 |
| 6,352,547 B1 | 3/2002 | Brown et al. ............ 606/198 |
| 6,360,577 B2 | 3/2002 | Austin ............ 72/402 |
| 6,387,117 B1 | 5/2002 | Arnold, Jr. et al. ............ 623/1.1 |
| 6,387,118 B1 | 5/2002 | Hanson ............ 623/1.11 |
| 6,481,262 B2 * | 11/2002 | Ching et al. ............ 72/416 |
| 6,568,235 B1 * | 5/2003 | Kokish ............ 72/402 |
| 6,629,350 B2 * | 10/2003 | Motsenbocker ............ 29/283.5 |
| 6,651,478 B1 | 11/2003 | Kokish ............ 72/402 |
| 6,666,880 B1 * | 12/2003 | Chiu et al. ............ 623/1.11 |
| 6,718,814 B2 * | 4/2004 | Bartrom et al. ............ 72/402 |
| 6,769,161 B2 | 8/2004 | Brown et al. ............ 29/234 |
| 6,823,576 B2 * | 11/2004 | Austin ............ 29/516 |
| 6,915,560 B2 * | 7/2005 | Austin ............ 29/722 |
| 6,968,607 B2 * | 11/2005 | Motsenbocker ............ 29/505 |
| 7,021,114 B2 * | 4/2006 | Perreault ............ 72/402 |
| 7,143,625 B2 * | 12/2006 | Edin ............ 72/402 |
| 7,207,204 B2 * | 4/2007 | Weber et al. ............ 72/402 |
| 7,225,518 B2 * | 6/2007 | Eidenschink et al. ............ 29/283.5 |
| 7,284,401 B2 * | 10/2007 | Larson et al. ............ 72/44 |
| 7,316,147 B2 * | 1/2008 | Perreault et al. ............ 72/402 |
| 7,487,579 B2 * | 2/2009 | Eidenschink et al. ............ 29/515 |
| 7,563,400 B2 * | 7/2009 | Wilson et al. ............ 264/249 |
| 7,578,041 B2 * | 8/2009 | Weber et al. ............ 29/515 |
| 7,587,801 B2 * | 9/2009 | Austin ............ 29/283.5 |
| 7,673,379 B1 * | 3/2010 | Pacetti ............ 29/447 |

(Continued)

*Primary Examiner* — Essama Omgba
(74) *Attorney, Agent, or Firm* — Seager Tufte & Wickhem LLC (57) ABSTRACT

A crimping system for crimping a stent onto a catheter balloon includes at least one crimping head of moveable contracting members, which define a diameter reduction chamber. The chamber has a length and a longitudinal axis. The chamber has a reduced diameter configuration and a pre-reduction diameter configuration. Each member has a length corresponding to the length of the chamber. In both the reduced diameter configuration and the pre-reduction diameter configuration each member is a given distance from the longitudinal axis, wherein a first region of the length of each member is a greater distance from the longitudinal axis than a second region of the length of each member.

20 Claims, 5 Drawing Sheets

U.S. PATENT DOCUMENTS

| | | | |
|---|---|---|---|
| 7,886,569 B2 * | 2/2011 | Weber et al. | 72/402 |
| 2002/0035774 A1 | 3/2002 | Austin | 29/516 |
| 2002/0107507 A1 | 8/2002 | Pinchasik | 606/1 |
| 2004/0078953 A1 | 4/2004 | Spilka | 29/505 |
| 2004/0177805 A1 * | 9/2004 | Hijlkema et al. | 118/101 |
| 2005/0119720 A1 | 6/2005 | Gale et al. | 623/1.11 |
| 2005/0188525 A1 | 9/2005 | Weber et al. | 29/508 |
| 2006/0229712 A1 * | 10/2006 | Wilson et al. | 623/1.42 |
| 2007/0006441 A1 * | 1/2007 | McNiven et al. | 29/508 |
| 2007/0204455 A1 * | 9/2007 | Knott et al. | 29/508 |
| 2009/0292347 A1 * | 11/2009 | Asmus et al. | 623/1.11 |
| 2011/0100086 A1 * | 5/2011 | Weber et al. | 72/402 |

* cited by examiner

CRIMPING AND EDGE PROTECTION ELEMENTS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention relates generally to stents, stent loading, stent contracting and stent delivery systems and their respective methods of use. Some embodiments of the invention are more specifically directed to the loading and crimping of a stent onto a delivery catheter.

2. Description of Related Art

A stent is a generally tubular device that is used to support a bodily lumen. A stent is typically delivered to a desired bodily location via a catheter. Often the stent is loaded onto a portion of the catheter, such as a balloon or other region of the catheter shaft. In some stent delivery systems the stent is crimped to the catheter in order to minimize the profile of the stent on the catheter and to prevent undesired movement of the stent relative to the catheter shaft.

Other techniques for crimping stents involve the use of mechanical devices for crimping stents. Mechanical stent crimpers have been disclosed in a number of patents including U.S. Pat. No. 6,769,161; U.S. Pat. No. 6,387,118; U.S. Pat. No. 6,387,117; U.S. Pat. No. 6,360,577; U.S. Pat. No. 6,352,547; U.S. Pat. No. 6,108,886; U.S. Pat. No. 6,092,273; U.S. Pat. No. 6,082,990; U.S. Pat. No. 6,074,381; U.S. Pat. No. 6,063,102 and U.S. Pat. No. 5,992,000.

Stent crimpers may have a variety of configurations and mechanisms for providing the stent diameter reduction chamber. For example, an iris type chamber wherein a plurality of members or blades are moved relative to the stent to reduce or expand the diameter of the chamber is described in U.S. Pat. No. 6,360,577, a crimper having a chamber defined by a plurality of member which extend inward to contract the chamber in a "star" or other geometric configuration is described in U.S. Pat. No. 6,168,921, a crimper having a pair of jaws or members that are moved relative to one another to reduce or expand the diameter of the chamber is described in U.S. Pat. No. 6,387,117, and a crimper having one or more conical apertures which at least partially define the chamber is described in U.S. Pat. No. 5,992,000. Crimpers having other configurations are also known. The entire content of each of the references cited above are incorporated herein by reference.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is particularly concerned with the crimping and otherwise reducing in size of stents, including bare or coated stents of any configuration or expansion type, including inflation expandable stents, self-expanding stents, hybrid expandable stents, etc. For the purpose of this disclosure, it is understood that the term 'stent' includes stents, stent-grafts, grafts, vena cava filters, expandable frame works, and other implantable medical devices for luminal placement. It is also understood that the term 'crimping' refers to a reduction in size or profile of a stent and 'crimper' refers to devices for accomplishing such reduction in size or profile of a stent.

The present invention is embodied in a variety of forms. In at least one embodiment the invention is directed to a stent reducing and/or loading mechanism such as a stent crimper and/or associated reducing and loading tools. In some embodiments a crimper comprises a crimping head having a contractible opening, iris or chamber defined by a plurality of members or blades which define the chamber. The chamber has a variable diameter and may be adjusted between an open diameter and a closed diameter.

In at least one embodiment two adjacent crimping heads are provided wherein the adjacent crimping heads define a single chamber extending therebetween, which has at least one stepped region of a diameter different than an adjacent region. In at least one embodiment a first crimping head defines a first region of the chamber having a first diameter and a second crimping head forms a second region of the chamber having a greater diameter than the first region.

In some embodiments the first region corresponds to the portion of the chamber defined by the first crimping head, and which is configured to come into contact with a stent. The second region is the portion or portions of the chamber defined by one or more second crimping heads, which is adjacent to one or both ends of the stent.

In at least one embodiment a single crimping head is utilized to provide the stepped chamber. In some embodiments the blades of the crimping head are configured to have a long section and a shorter section. The long section corresponds to the first region of the chamber and the short section corresponds to the second region of the chamber.

In at least one embodiment the blades or portions of the blades of a given crimping head that are configured to contact the balloon or portions of the catheter adjacent to the stent during crimping are heated relative to blades or portions of blades adjacent thereto.

In at least one embodiment the blades or portions of the blades of a given crimping head that are configured to contact the stent during crimping are heated or cooled relative to blades or portions of blades adjacent thereto.

In at least one embodiment the blades or portions of the blades of a given crimping head that are configured to contact the stent during crimping are constructed of a conductive material, non-conductive material, and/or insulated material.

In at least one embodiment the blades or portions of the blades of a given crimping head that are configured to contact the balloon or portions of the catheter adjacent to the stent during crimping are constructed of a temperature insulating and/or temperature conducting material.

In at least one embodiment a stent is crimped onto a balloon catheter using one or more crimping heads which define a stepped crimping chamber.

In at least one embodiment a stent being crimped is coated with at least one therapeutic agent or drug.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, and/or substituted for, elements depicted in another figure as desired.

As indicated above, the present invention is embodied in a variety of forms. In at least one embodiment, such as for example in the embodiment depicted in FIG. 1, the invention is directed to a radial stent reducing assembly or crimper 10. Crimper 10 may have any configuration of contacting members and/or any configuration of stent diameter reducing chamber, such as has been described above.

Figure 1:
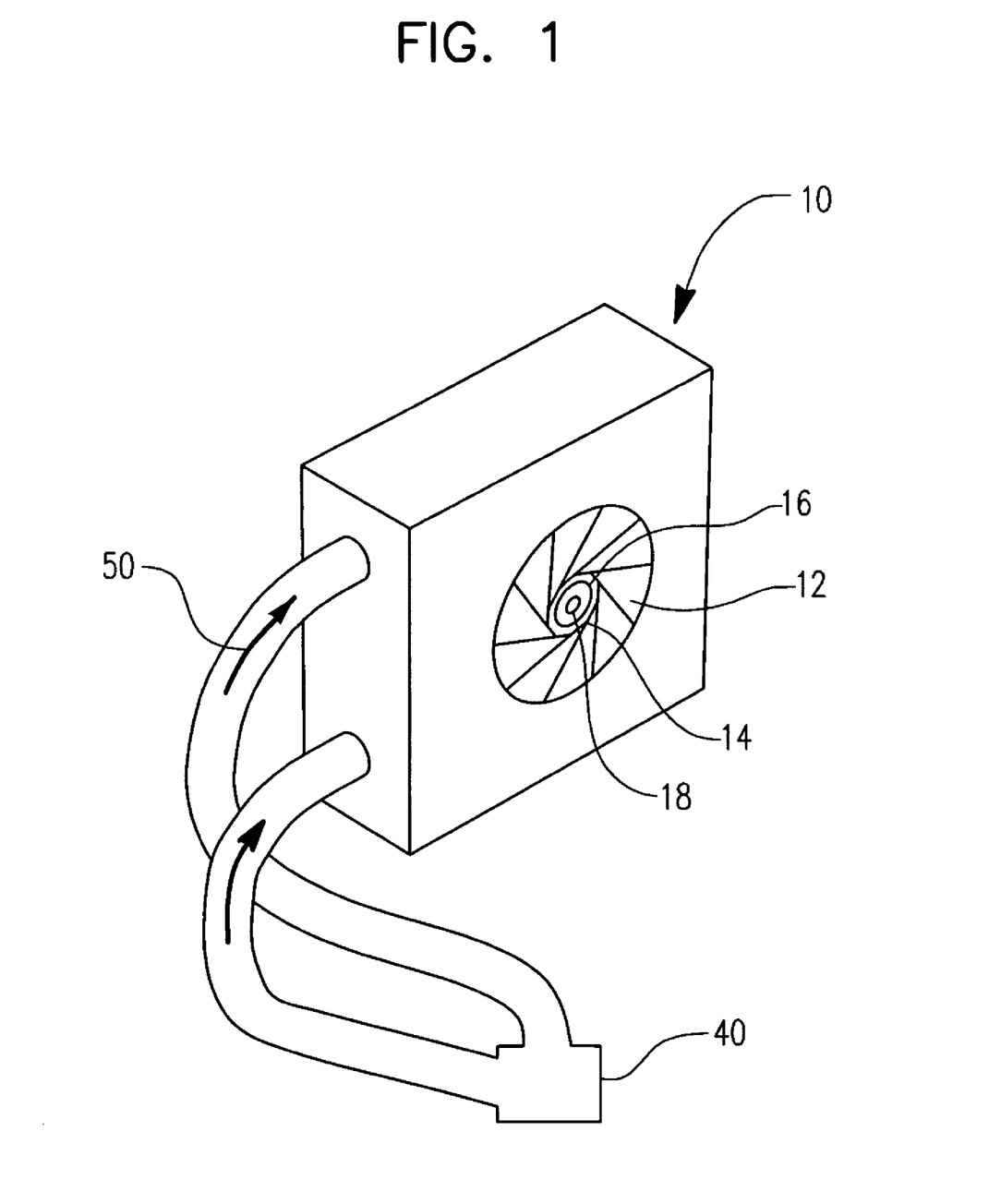
FIG. 1 is a perspective view of an embodiment of the invention wherein the stent reduction chamber is shown in the open or pre-reduction state.
Figure 2:
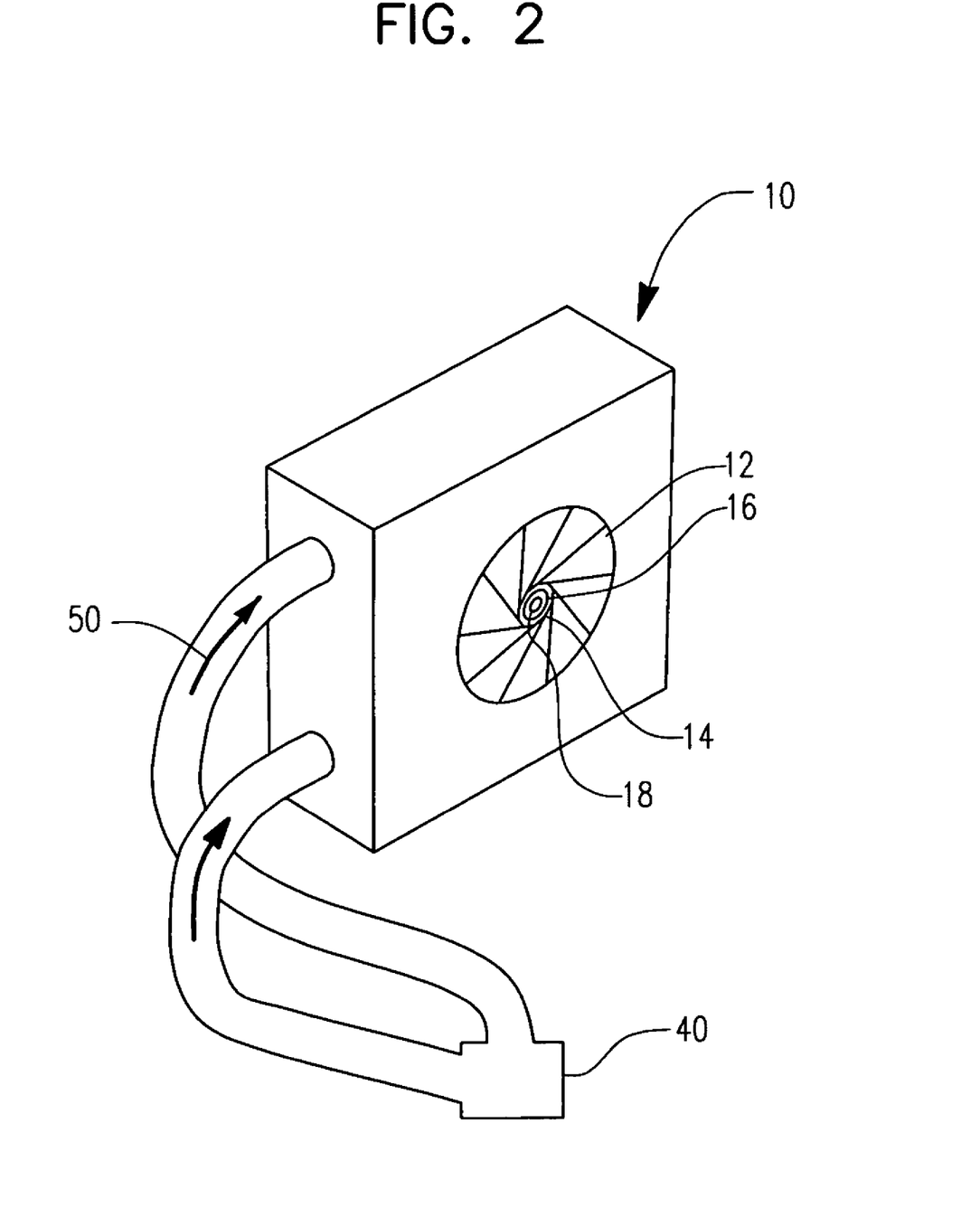
FIG. 2 is a perspective view of the embodiment shown in FIG. 1 wherein the chamber is shown in the closed or reduced state.

In the embodiment shown, crimper 10 is provided with a plurality of stent reducing members or blades 12 which define a stent reduction chamber 14 into which a stent or other medical device 16 is positioned in order to reduce the stent 16 from an unreduced diameter state, such as is shown in FIG. 1 to a reduced diameter state as is shown in FIG. 2.

In at least one embodiment the crimper comprises 8 to 20 blades. In at least one embodiment the crimper comprises 10 to 15 blades. In at least one embodiment the crimper comprises 12 blades.

Figure 3:
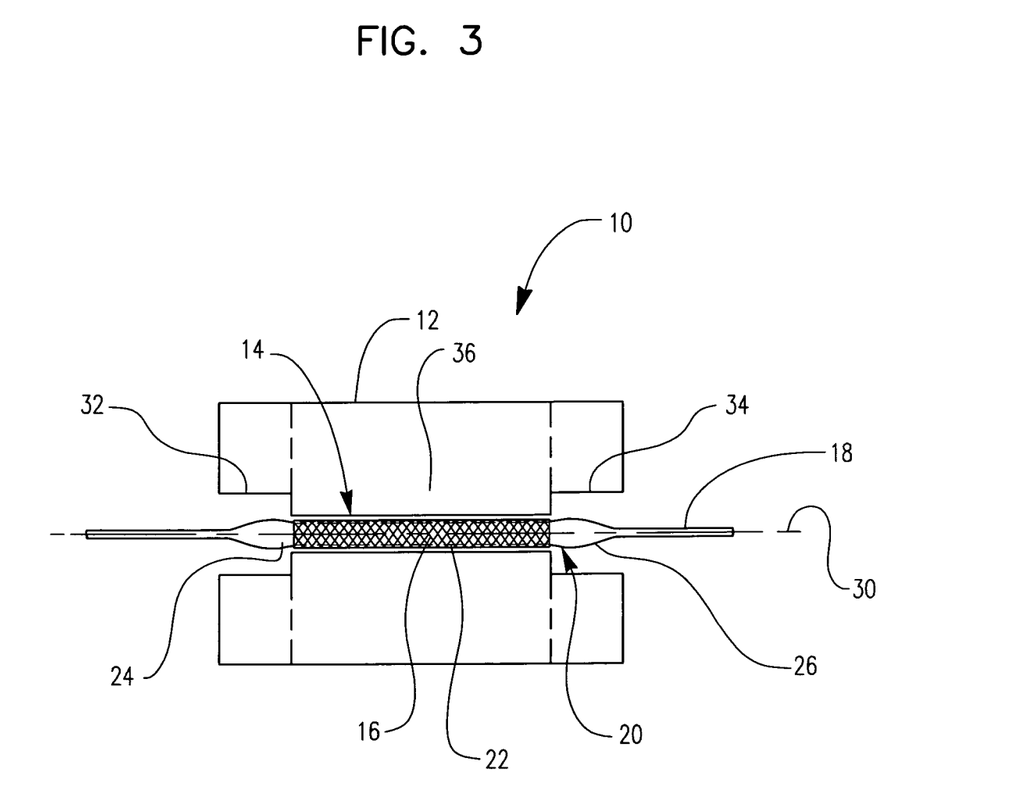
FIG. 3 is a partial longitudinal cross-sectional side view of the embodiment shown in FIG. 2.

In some embodiments, a stent 16 may be crimped on to a stent delivery catheter 18 utilizing the crimper 10, such as in the manner shown in FIGS. 1-3. In the case of a balloon expandable stent, the catheter 18 will include a balloon 20, such as is shown in FIG. 3. In some embodiments the stent 16 will typically be mounted on the working portion or body 22 of the balloon 20, which extends between the proximal and distal cones 24 and 26 of the balloon 20. In some embodiments, prior to loading the pre-crimped stent 16 onto the balloon 20, the balloon is folded or wrapped about the shaft 28 of the catheter 18 in a reduced pre-deployment state.

As is shown in FIG. 3 the chamber 14 is defined by the relative position of each member or blades 12. The length of the blades 12 correspond to the length of the chamber 14. In at least one embodiment, one or more regions along the length of each blade has a height or distance from a longitudinal axis 30 of the chamber, which is greater than a region of the blade adjacent thereto. For example, in the embodiment shown in FIG. 3 end regions 32 and 34 of the length of each member 12 is a greater distance from the longitudinal axis 30 than the medial region 36 of the blade what extends therebetween. In other words the end regions 32 and 34 are differentiated from the region 36 by the step in relative distance from the longitudinal axis 30 shown.

This unique configuration of blades 12, which define the chamber 14 has a variety of effects.

For instance, during the crimping process, as the chamber 14 is transitioned from the pre-reduced diameter configuration to the reduced diameter configuration, the region 36 (which in the embodiment shown is disposed about only the portion of the catheter 18 corresponding to the stent 16) will exert a radially inward force on only the stent 16 and/or the working portion 22 of the balloon 20 to crimp the stent 16 onto the balloon 20. As shown in FIG. 3 regions 32 and 34 are maintained a further distance away from the catheter 18 during the crimping procedure. As a result, the cones 24 and 26 of the balloon, about which the regions 32 and 34 are respectively disposed, may be inflated, heat-set or otherwise manipulated during the crimping process, without being reduced by contact with the blades 12.

In at least one embodiment, during the crimping process, one or both regions 32 and 34 may be heated by a heat source 40, such as is depicted in FIGS. 1 and 2. Heat source 40 is operatively engaged to one or both regions 32 and 34 to conductively or otherwise transmit heat (depicted by arrows 50) to the region(s) as desired.

Because it may be the case that the stent 16 is coated with one or more coatings and/or therapeutic agents, such as a drug, genetic component, etc., which may be sensitive to or adversely affected by excess heat, in some embodiments the region of the blade 12 that is configured for contact with the stent 16 is constructed from or provided with a heat insulating material such as any of a variety of suitable polymers, carbon, non or minimally conductive metals, ceramics, etc.

In at least one embodiment the region of the blade 12 that is configured to contact the stent 16 is at least partially constructed of a temperature conducting material such as stainless steel or one or more alloys thereof.

In some embodiments a region or regions of the blade 12, which are configured to be disposed about the cones 24 and 26 of the balloon 20, are constructed of a heat conducting material such as one or more conductive metals, for example: stainless steel and/or alloys thereof.

Figure 4:
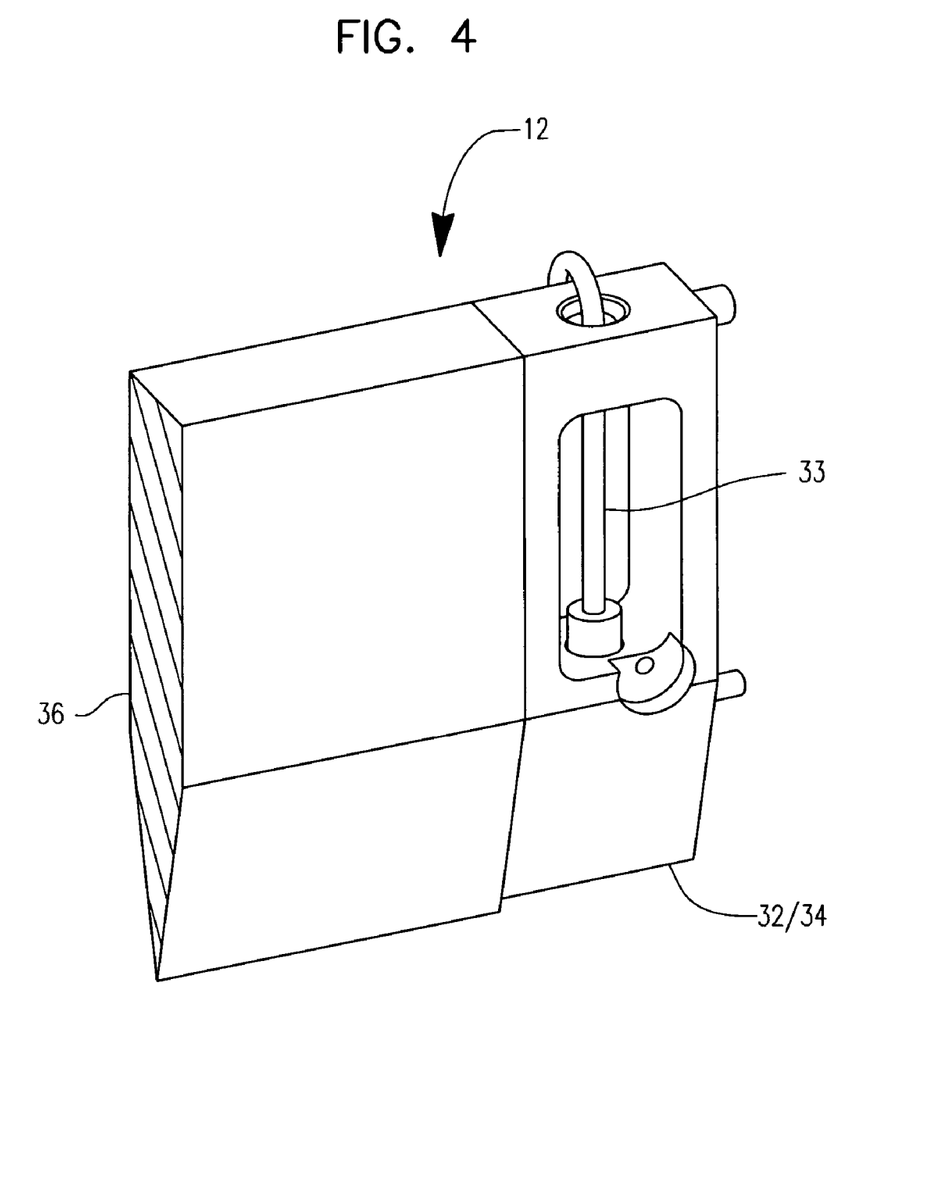
FIG. 4 is a an enlarged view of a crimping member or blade shown in FIGS. 1-3.

In at least one embodiment, an example of which is shown in FIG. 4, a given blade 12 comprises a first region 32/34 constructed of a heat conducting material and a second region 36 constructed of a heat insulating material. Region 32/34 may be operatively engaged to a heat source such as previously described.

As indicated above, by heating the stepped region or regions of the blades 12 which are disposed about the cones 24 and 26, the cones may be heat-set during the crimping process.

In at least one embodiment, at least a portion of the blade 12, such as for example first region 32/34, is configured to allow a heated fluid such as a liquid or gas (e.g.: heated air, etc.) to be blown through the stepped regions 32/34 and directly onto the cones 24/26. In such embodiments the region 32/34 define one or more fluid transfer lumens 33, of which one is shown in FIG. 4, that are in fluid communication with the heat source, such as in the manner shown in FIGS. 1 and 2.

In at least one embodiment, the balloon 20 is partially pressurized to allow the cones to "puff" out relative to their un-inflated configuration, while the stent 16 is being crimped by region 36 of the blades. The regions 32 and 34 of the blades 12 disposed about the respective balloon cones 24 and 26 are then heated in the manner previously described to set the cones in their "puffed" configuration such as in the manner depicted in FIG. 5.

Figure 5:
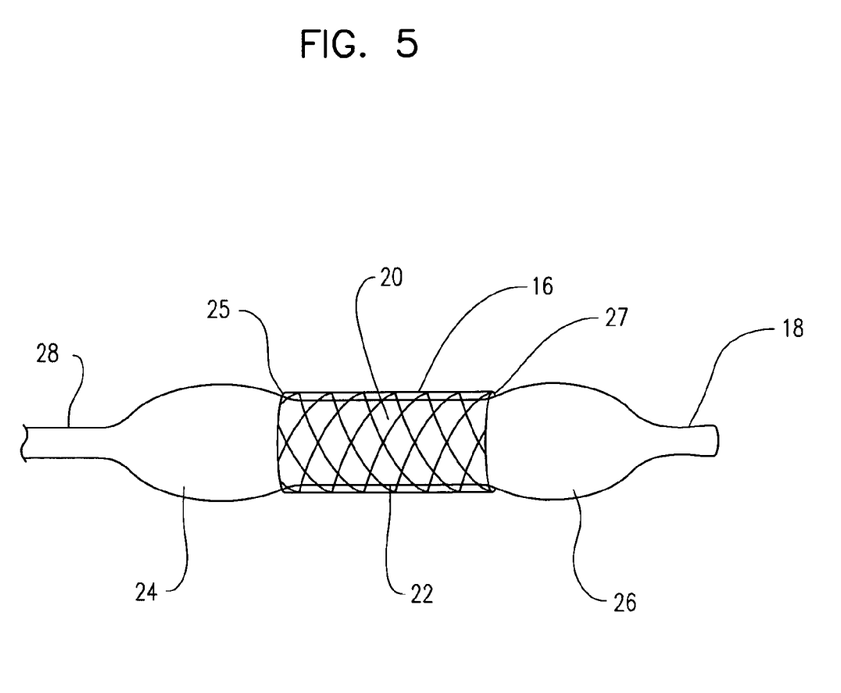
FIG. 5 is a perspective view of a balloon having a stent mounted thereon shown following a crimping and heat setting process.

By heat setting the cones 24 and 26 of the balloon 20 in this manner, the edges 25 and 27 of the stent 16 may be protected by the "puffed" cones 24 and 26 which partially abut and overlap the respective edges 25 and 27 of the stent 16 in a desired manner, such as is shown in FIG. 5.

The temperature and duration of the heat cycle will vary, and is determined at least in part by the specific polymeric structure and characteristics of the cones.

As indicated above, though heat is transmitted through the regions 32 and 34 of the blades 12 during the crimping process depicted in FIG. 3, the insulated region 36 of the blades 12 remains substantially unaffected by the transmission of heat to the adjacent regions. In some embodiments however, if desired, the region 36 of one or more blades 12 may also be configured and/or constructed to conduct heat.

In at least one embodiment a coolant fluid, such as a liquid or gas may be selectively applied to one or more regions of the blade 12, and/or to the stent 16 directly, if desired.

Rather than provide for a single crimping head having blades of a stepped height configuration such as is shown in FIGS. 3 and 4, in at least one embodiment of the invention multiple crimping heads are utilized which have proportionally different diameter crimping chambers in both the pre-reduction diameter configuration and the reduced diameter configuration. When such crimping heads are placed immediately adjacent to one another, the respective crimping chambers effectively form a single stepped diameter chamber, with the number and size of each step dependent on the size of each chamber. It will be recognized that any of a variety of stepped configurations may be provided to a crimping chamber in this manner.

In some embodiments the stent 16, the delivery system or other portion of the catheter assembly 18 may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

As indicated above, the crimper 10 shown and described above, is particularly suited for use with stent having one or more coatings or other mechanisms for the delivery of a therapeutic agent.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:
1. A crimping system comprising:
a crimper including at least one crimping head, the at least one crimping head comprising a plurality of radially moveable contracting members, the plurality of contracting members defining a diameter reduction chamber, the chamber having a length and a longitudinal axis, the chamber having a reduced diameter configuration and a pre-reduction diameter configuration, each member having a length, the length of each member corresponding to the length of the chamber, in both the reduced diameter configuration and the pre-reduction diameter configuration each member being positioned a distance from the longitudinal axis, wherein a first region of the length of each member is a greater distance from the longitudinal axis than a second region of the length of each member, a heat source for operatively heating the first region of at least one of the plurality of moveable contracting members, and a coolant for operatively cooling the second region of the at least one of the plurality of moveable contracting members while the heat source operatively heats the first region.

2. The system of claim 1 wherein the first region and the second region are separated by a step.

3. The system of claim 1 wherein the first region of each member includes a temperature conducting material and the second region of each member includes a temperature insulating material, wherein the temperature insulating material is selected from at least one member of the group consisting of ceramics, polymeric materials, carbon, and any combination thereof.

4. The system of claim 1 wherein the first region of each member is constructed of stainless steel or an alloy thereof.

5. The system of claim 1, wherein the heat source is conductively engaged to the first region.

6. The system of claim 1 comprising a first crimping head and a second crimping head positioned adjacent thereto.

7. The system of claim 1 wherein the first region of each member includes a temperature conducting material.

8. The system of claim 7 wherein the second region of each member includes a temperature insulating material.

9. The system of claim 7 wherein the second region of each member includes a temperature conducting material.

10. A crimping system for crimping a stent onto a catheter balloon, comprising:
    a crimper including a crimping head including a plurality of movable contracting members radially arranged to collectively define a stent reduction chamber, wherein the plurality of movable contracting members are actuatable to radially reduce the size of the stent reduction chamber during a stent crimping process;
    wherein each of the plurality of movable contracting members includes a first end region, a second end region and a medial region intermediate the first end region and the second end region;
    a coolant for operatively cooling the medial regions of the movable contracting members while actuating the contracting members during the stent crimping process; and
    a heating source for operatively heating the first end regions and the second end regions of the movable contracting members while actuating the contracting members during the stent crimping process;
    wherein the medial regions are configured to contact a stent positioned in the stent reduction chamber during the crimping process while cooling the medial regions and heating the first end regions and the second end regions.

11. The crimping system of claim 10, further comprising:
    a balloon; and
    a stent mounted on the balloon;
    wherein the stent and balloon are positioned in the stent reduction chamber.

12. The crimping system of claim 11 wherein heat from the heating source is transmitted to the balloon.

13. The crimping system of claim 12 wherein the balloon is partially inflated within the stent.

14. The crimping system of claim 13 wherein the stent is cooled by the coolant.

15. The crimping system of claim 14 wherein the stent is coated with a therapeutic agent.

16. The crimping system of claim 15 wherein the medial regions of the movable contracting members exert a radially inward force on the stent.

17. The crimping system of claim 16 wherein the stent reduction chamber has a length and a central longitudinal axis, and wherein the first end region and the second end region of each movable contracting member are a greater distance from the central longitudinal axis than the medial region of each movable contracting member.

18. A crimping system for crimping a stent onto a catheter balloon, comprising:
    a crimper including a crimping head including a plurality of movable contracting members radially arranged to collectively define a stent reduction chamber, wherein the plurality of movable contracting members are actuatable to radially reduce the size of the stent reduction chamber;
    a balloon catheter including a balloon;
    a stent loaded onto the balloon of the balloon catheter;
    wherein the balloon and the stent are positioned in the stent reduction chamber;
    a coolant for operatively cooling the stent in the stent reduction chamber; and
    a heating source for operatively heating the balloon in the stent reduction chamber;
    wherein the stent is cooled and the balloon is heated as the plurality of movable contracting members exert a radially inward force on the stent in the stent reduction chamber.

19. The crimping system of claim 18 wherein the stent is coated with a therapeutic agent.

20. The crimping system of claim 19 wherein the balloon is partially inflated within the stent.

* * * * *